(12) United States Patent
Kang et al.

(10) Patent No.: US 10,877,260 B2
(45) Date of Patent: Dec. 29, 2020

(54) ELECTROSTATIC TOUCH ASSEMBLY OF LIGHT SOURCE DEVICE FOR ENDOSCOPE AND ENDOSCOPE SYSTEM INCLUDING THE SAME

(71) Applicant: INTHESMART Inc., Seoul (KR)

(72) Inventors: Uk Kang, Seoul (KR); Ilhyung Shin, Jeju (KR)

(73) Assignee: INTHESMART CO., LTD., Seoul (KR)

( * ) Notice: Subject to any disclaimer, the term of this patent is extended or adjusted under 35 U.S.C. 154(b) by 117 days.

(21) Appl. No.: 15/648,409

(22) Filed: Jul. 12, 2017

(65) Prior Publication Data

US 2018/0329198 A1 Nov. 15, 2018

(30) Foreign Application Priority Data

May 10, 2017 (KR) ........................ 10-2017-0057980

(51) Int. Cl.
| | | |
|---|---|---|
| *A61B 1/05* | (2006.01) | |
| *A61B 1/06* | (2006.01) | |
| *A61B 1/07* | (2006.01) | |
| *A61B 5/00* | (2006.01) | |
| *H05B 37/02* | (2006.01) | |
| *G02B 23/24* | (2006.01) | |
| *A61B 1/00* | (2006.01) | |
| *H05B 47/105* | (2020.01) | |

(52) U.S. Cl.
CPC ...... *G02B 23/2407* (2013.01); *A61B 1/00006* (2013.01); *A61B 1/0011* (2013.01); *A61B 1/00039* (2013.01); *A61B 1/00048* (2013.01); *A61B 1/0669* (2013.01); *A61B 1/0684* (2013.01); *A61B 1/07* (2013.01); *A61B 5/0086* (2013.01); *G02B 23/2476* (2013.01); *A61B 1/05* (2013.01); *H05B 47/105* (2020.01)

(58) Field of Classification Search
CPC ............ H05B 37/0227; H05B 37/0218; A61B 1/00006; A61B 1/00039; A61B 1/00048; A61B 1/0011; A61B 1/05; A61B 1/0669; A61B 1/0684; A61B 1/07; A61B 5/0086; G02B 23/2476; G02B 23/2407
See application file for complete search history.

(56) References Cited

U.S. PATENT DOCUMENTS 3,621,268 A * 11/1971 Friedrich ........... H03K 17/9631
  250/214.1
7,656,393 B2 * 2/2010 King ...................... G06F 1/1626
  345/173

(Continued)

*Primary Examiner* — Arman B Fallahkhair
(74) *Attorney, Agent, or Firm* — Patent Office of Dr. Chung Park

(57) ABSTRACT

Disclosed is a light source device for endoscope including: a front panel which includes a touch portion and a display portion; a touch board which is disposed in a rear side of the front panel, and comprises an electrostatic touch sensor that is located in a position corresponding to the touch portion and detects an input generated in the touch portion; a light source board which is disposed in a rear side of the touch board, and comprises a light source configured to irradiate light to at least one of the display portion and the touch portion; and a guide unit which is provided between the touch board and the light source board, and guides the light irradiated from the light source.

7 Claims, 10 Drawing Sheets

(56) References Cited

U.S. PATENT DOCUMENTS

| | | | | |
|---|---|---|---|---|
| 7,705,257 B2* | 4/2010 | Arione | ............... | H03K 17/962 |
| | | | | 200/314 |
| 8,063,326 B2* | 11/2011 | Igarashi | ............... | H01H 13/83 |
| | | | | 200/310 |
| 8,587,561 B2* | 11/2013 | Kim | ............... | G06F 3/042 |
| | | | | 345/173 |
| 8,605,960 B2* | 12/2013 | Orsley | ............... | G06F 3/0421 |
| | | | | 382/124 |
| 9,709,284 B2* | 7/2017 | Bach | ............... | F24C 7/083 |
| 10,149,599 B2* | 12/2018 | Ito | ............... | G01N 21/27 |

* cited by examiner

[Fig. 1]
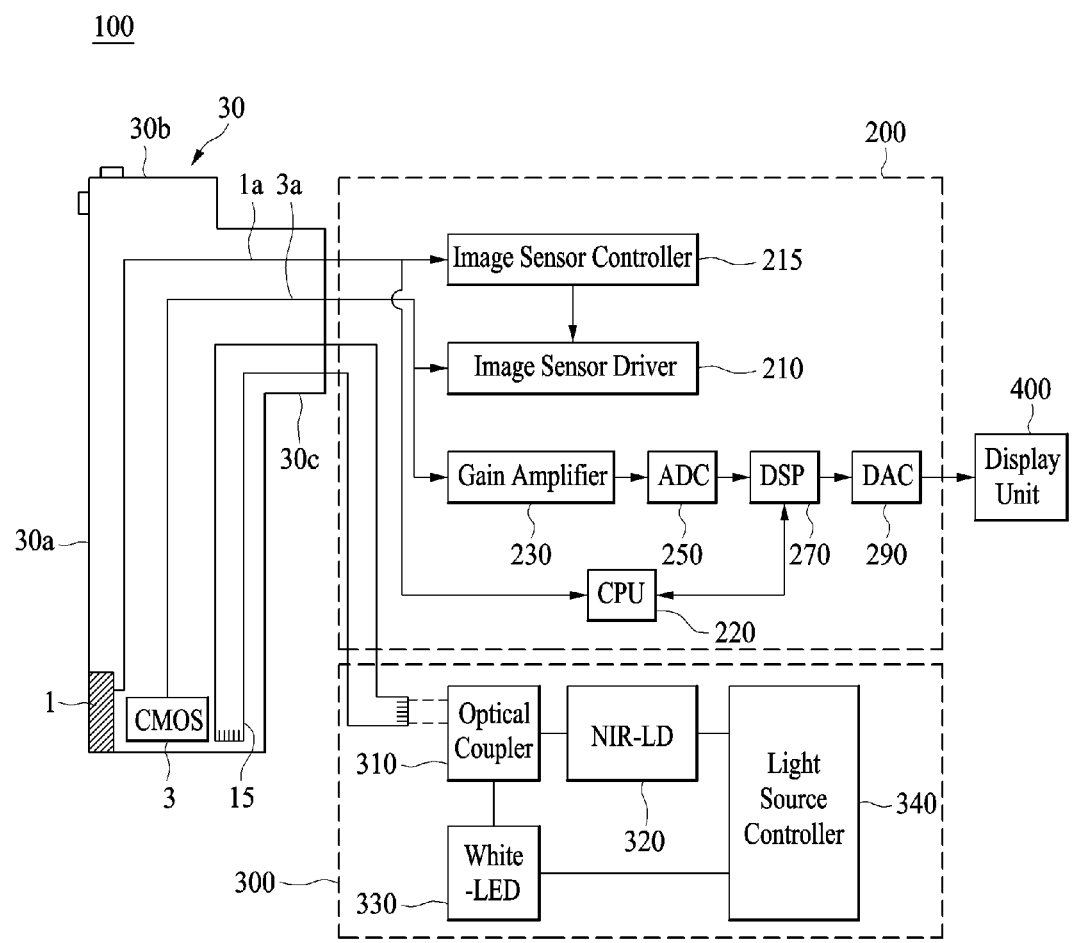

[Fig. 2]
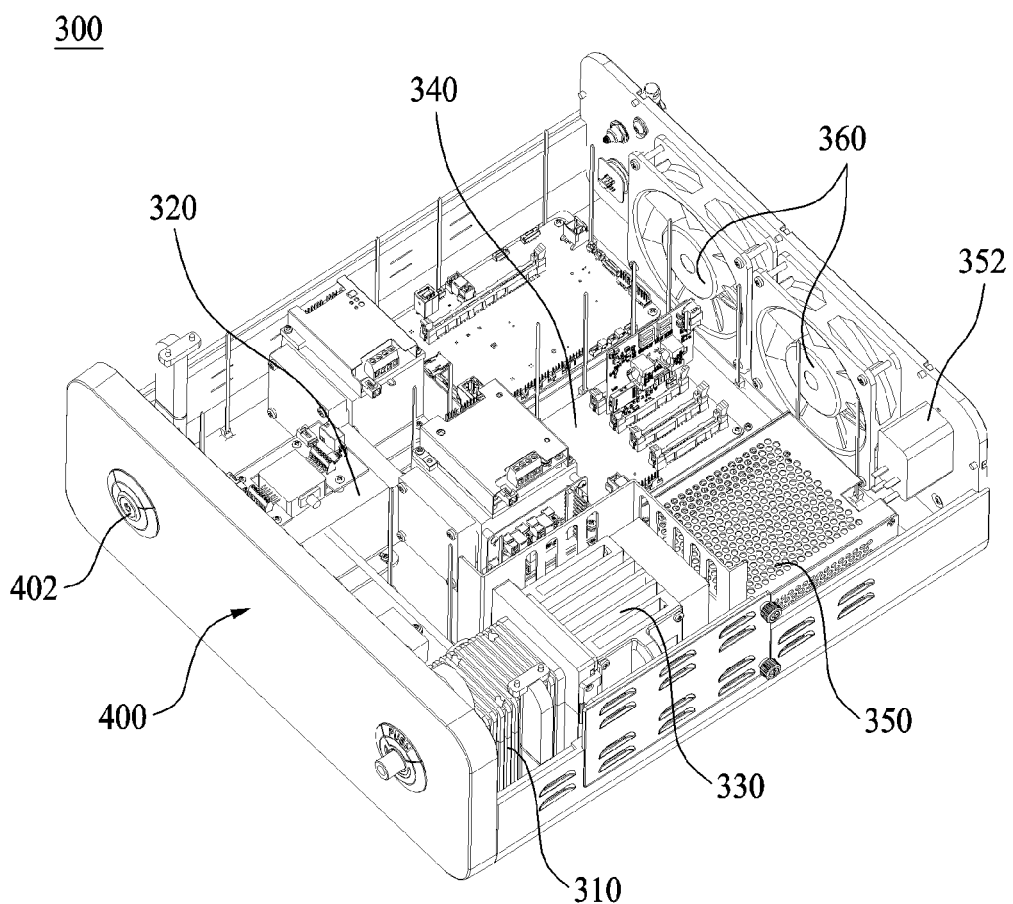

[Fig. 3]
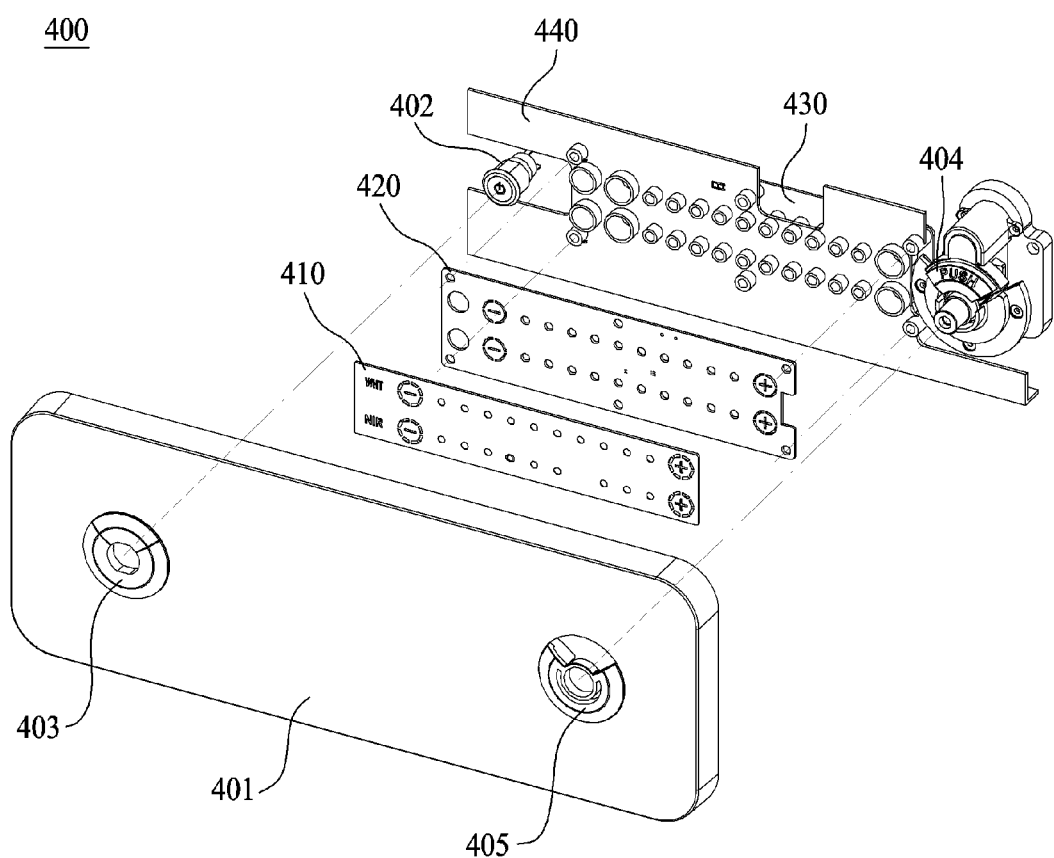

[Fig. 4]
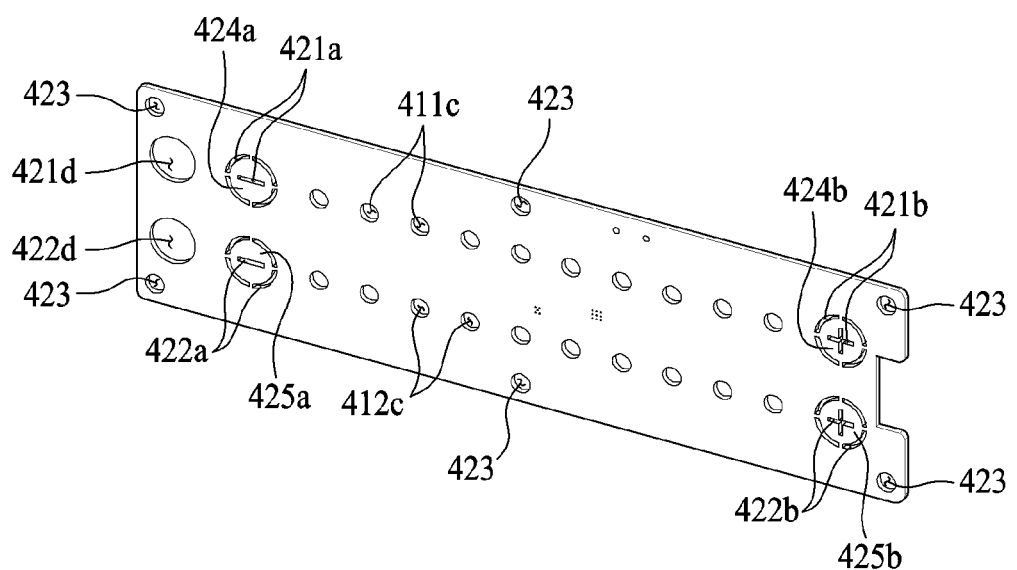

[Fig. 5]
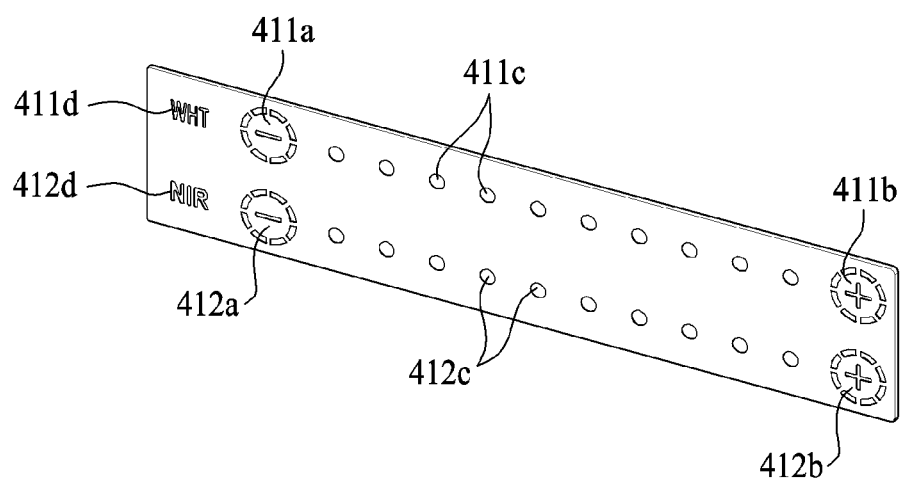

[Fig. 6]
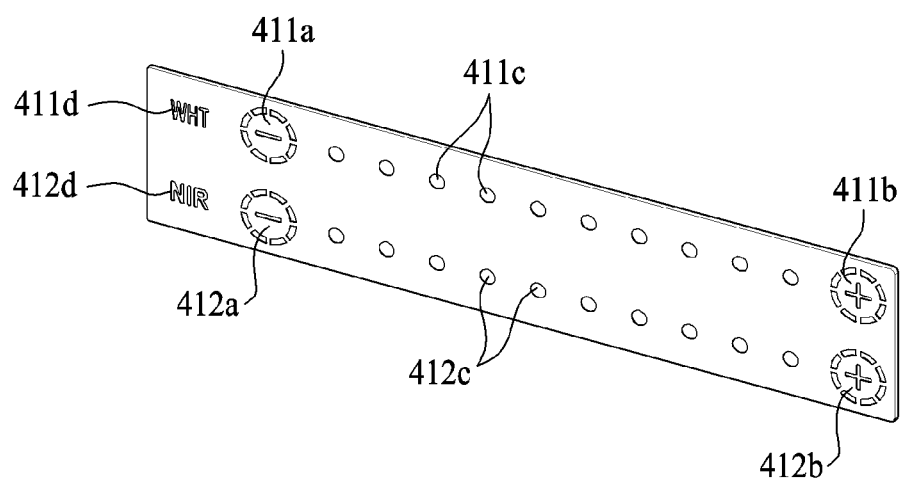

[Fig. 7]
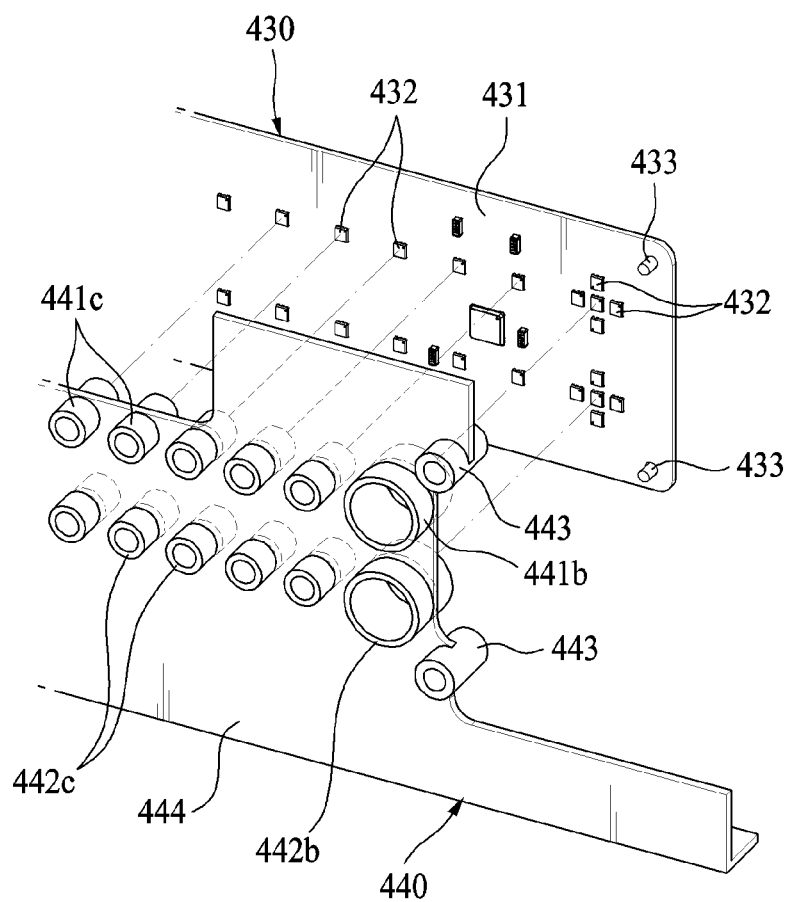

[Fig. 8]
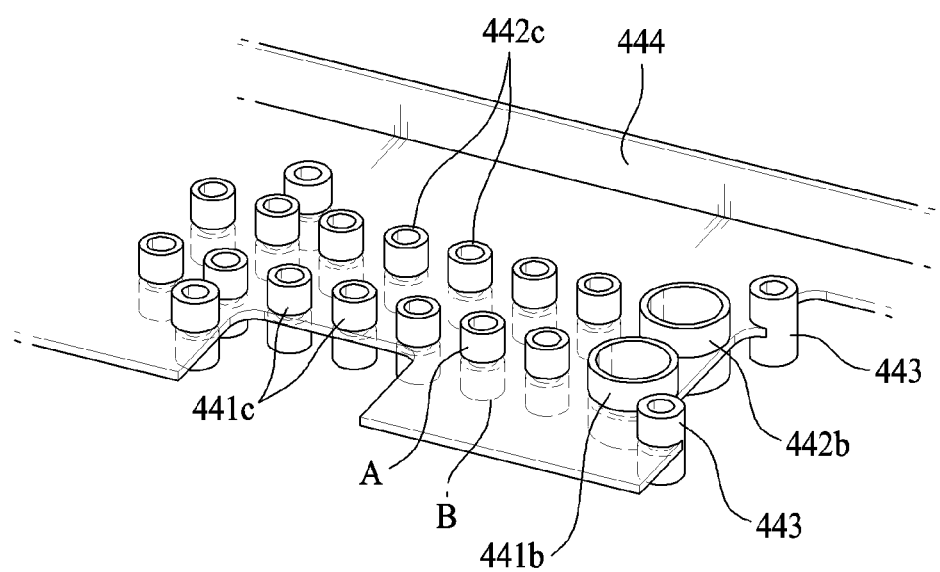

[Fig. 9]
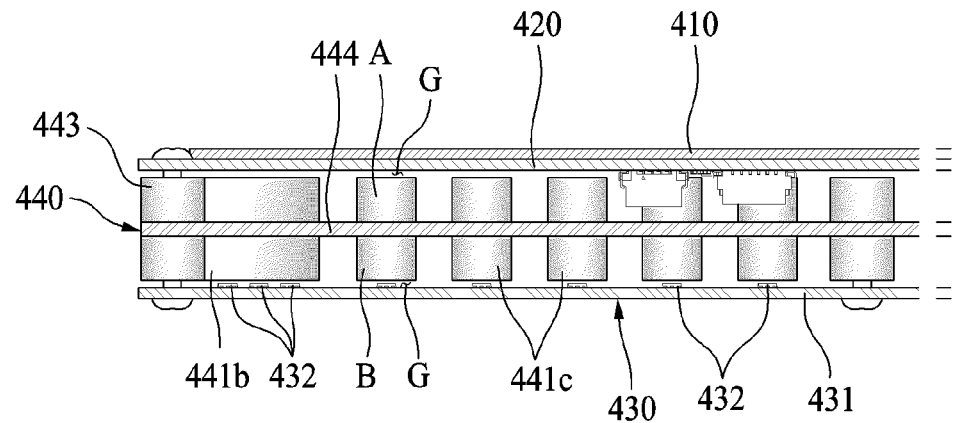
[Fig. 10]
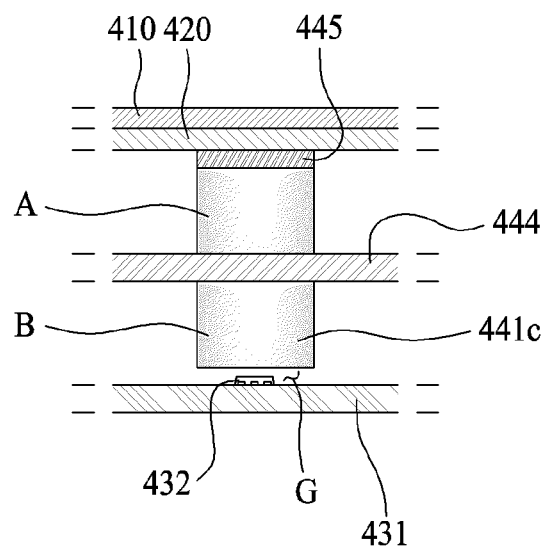

[Fig. 11]
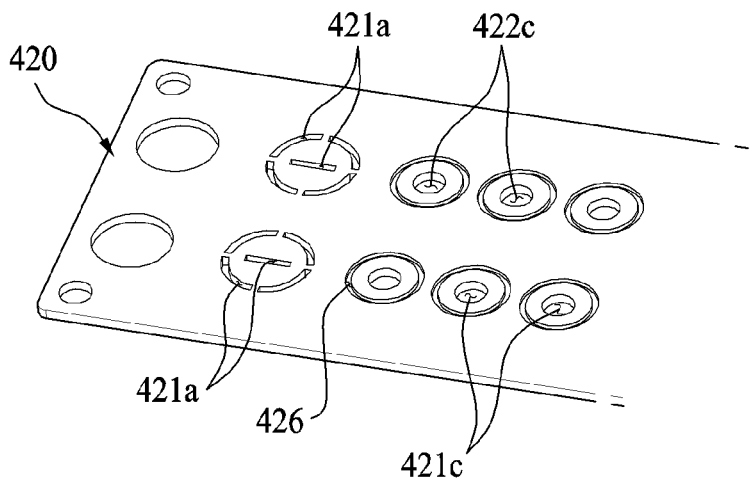
[Fig. 12]
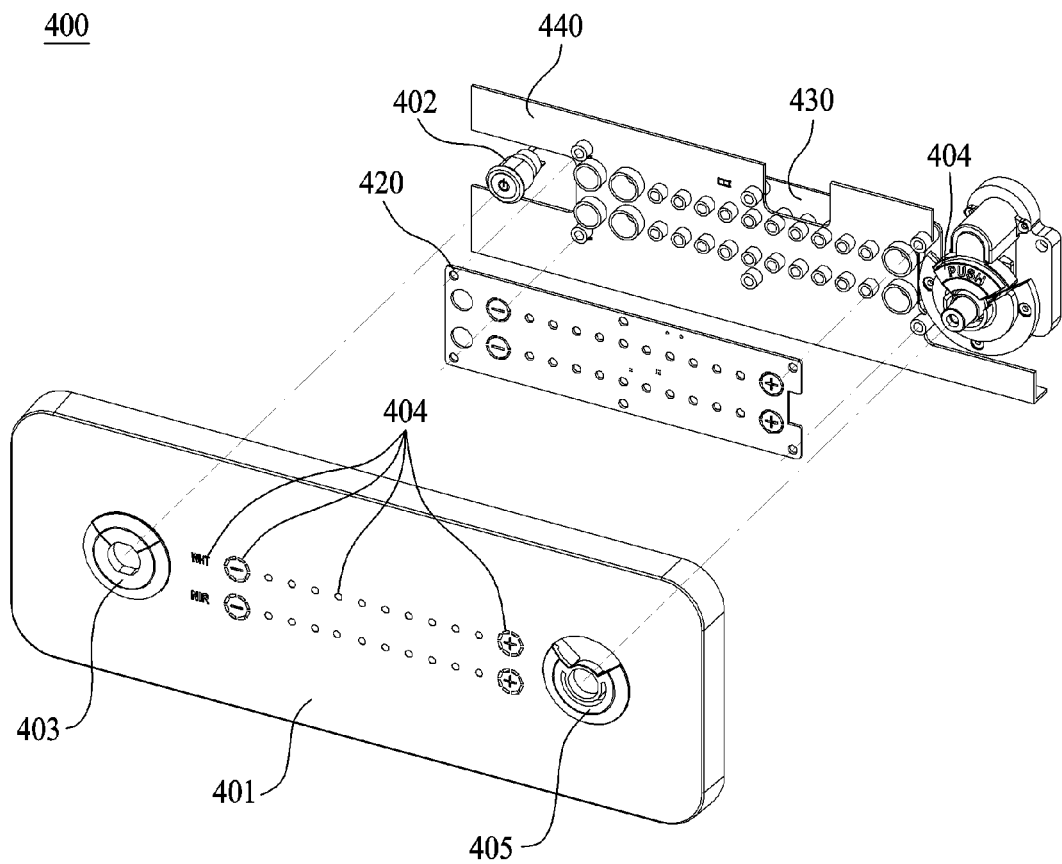

ELECTROSTATIC TOUCH ASSEMBLY OF LIGHT SOURCE DEVICE FOR ENDOSCOPE AND ENDOSCOPE SYSTEM INCLUDING THE SAME

CROSS-REFERENCE TO RELATED APPLICATIONS

This application claims priority under 35 U.S.C. § 119 from Korean Application No. 10-2017-0057980 filed on May 10, 2017, the subject matter of which is incorporated herein by reference.

BACKGROUND OF THE INVENTION

Field of the Invention

The present invention relates to an auxiliary device for endoscope, and more particularly, to an electrostatic touch assembly applied to a light source device and an endoscope including the same.

Description of the Related Art

An endoscope is a device that can capture an image and monitor narrow spaces such as the inside of a human body and the inside of a machine. It can be used not only in a medical field, but also in various industrial fields such as monitoring the inside of a precision machine without disassembling and monitoring abnormality in the inside of a pipe.

Particularly, in the medical field, the endoscope can monitor the inside of a human body (stomach, bronchus, esophagus, large intestine, small intestine, etc.) by using a small-sized camera without the ventrotomy or incision of body such as surgery or autopsy, or by passing through a part of body to monitor the inside of the abdominal cavity so that it can check whether any abnormal exists.

A well-known conventional endoscope system includes, in a fore-end of the endoscope, a light source device for irradiating light to view the internal organs of body or the inside surface of a machine, an image sensor for receiving a light signal which is irradiated from the light source device is reflected from the surface of internal organ of human body after being projected and converting the received light signal into an electrical signal (image signal), and a camera with a camera chip including an encoder for converting the image signal into an electronic signal so that the image signal can be monitored through a monitor.

Particularly, the light source device is provided with a button unit for controlling the light source through an operation, and the button unit may be implemented in the form of a pressure sensitive type touch pad using a pressure sensitive sensor in addition to a general physical button.

However, in the case of such a pressure sensitive type touch pad, there is an advantage that it is inexpensive and easy to apply because touch can be determined by sensing a physical pressure. However, there is a problem in that the reaction speed is low and the input cannot be achieved when user performs the operation with a force below a reference pressure value. Accordingly, such a button unit of pressure sensitive type touch pad has a limitation in a medical field in which quick and precise operations should be performed.

In order to compensate for the disadvantages of the pressure sensitive type touch pad, a method of applying an electrostatic type touch pad to a button unit may be considered. However, in the electrostatic type touch pad, malfunction occurs or breakdown easily occurs in various unexpected situations such as an electric leakage, a power failure, an overcurrent flow, or the like, so that it is not easy to apply the electrostatic type touch pad to the medical field.

In particular, such a touch pad generally includes a light source for button to irradiate light so that the touch pad can be operated even in a dark environment, and the electrostatic type touch pad is difficult to be electrically separated completely from the light source for button. Therefore, the risk of malfunction and breakdown becomes greater.

SUMMARY OF THE INVENTION

The present invention has been made in view of the above problems, and provides an electrostatic touch assembly of light source device for endoscope capable of performing a quick and accurate input by applying an electrostatic touch method as a button input method applied to a light source device for endoscope, and fundamentally preventing malfunction and breakdown due to various electric unexpected situations and a endoscope including the same.

In accordance with an aspect of the present invention, a light source device for endoscope includes a front panel which includes a touch portion and a display portion; a touch board which is disposed in a rear side of the front panel, and comprises an electrostatic touch sensor that is located in a position corresponding to the touch portion and detects an input generated in the touch portion; a light source board which is disposed in a rear side of the touch board, and comprises a light source configured to irradiate light to at least one of the display portion and the touch portion; and a guide unit which is provided between the touch board and the light source board, and guides the light irradiated from the light source.

The guide unit includes a guide member which is formed to be elongated between the touch board and the light source board in a front-rear direction, has a hollow through which the light irradiated from the light source passes, and has a front end spaced apart from the touch board and a rear end spaced apart from the light source board.

The light source device for endoscope further includes a support member which is provided in at least one of the front end and the rear end of the guide member and has an insulation.

A support member is provided at the front end of the guide member, and a seating groove in which the supporting member is seated is formed on a rear surface of the touch board.

The guide unit includes a fixing plate which is fixed between the touch board and the light source board and fixes the guide member.

The guide unit includes a fixing member which is connected between the touch board and the light source board to fix the fixing plate while being fixed to the fixing plate.

At least one of the fixing plate and the fixing member has an insulation.

The touch board includes a through hole for passing the light irradiated from the light source so that light can be irradiated to the display portion or the touch portion.

The light source device for endoscope further includes a white light source module and a near infrared light source module, wherein the touch board includes: a first touch sensor for white light source module configured to control to weaken a light of the white light source module; a second touch sensor for white light source module configured to strengthen a light of the white light source module; a first touch sensor for near infrared light source module configured to control to weaken a light of the near infrared light source module; and a second touch sensor for near infrared light source module configured to strengthen a light of the near infrared light source module.

The through hole is formed in an area of the first touch sensor for white light source module, the second touch sensor for white light source module, the first touch sensor for near infrared light source module, and the second touch sensor for near infrared light source module.

The light source device for endoscope further includes a masking plate which is disposed between the front panel and the touch board and has impermeability of light in a remaining area excluding an area corresponding to the through hole.

The masking plate is processed by silk printing in the remaining area excluding the area corresponding to the through hole.

A surface of the front panel is coated with an opaque material, and a non-masking pattern is formed in the area corresponding to the through hole.

BRIEF DESCRIPTION OF THE DRAWINGS

The objects, features and advantages of the present invention will be more apparent from the following detailed description in conjunction with the accompanying drawings, in which:

FIG. 1 is a schematic diagram of an endoscope system according to a first embodiment of the present invention;

FIG. 2 is a diagram illustrating an internal structure of a light source device applied to the endoscope system according to the first embodiment of the present invention;

FIG. 3 is a diagram illustrating a constituent element of an electrostatic touch assembly of the light source device for endoscope according to the first embodiment of the present invention;

FIG. 4 is a diagram illustrating a touch board in the electrostatic touch assembly of the light source device for endoscope according to the first embodiment of the present invention;

FIG. 5 is a diagram illustrating a masking plate in the electrostatic touch assembly of the light source device for endoscope according to the first embodiment of the present invention;

FIG. 6 and FIG. 7 are diagrams illustrating a guide unit and a light source board in the electrostatic touch assembly of the light source device for endoscope according to the first embodiment of the present invention;

FIG. 8 and FIG. 9 are diagrams illustrating a structure of the guide unit in the electrostatic touch assembly of the light source device for endoscope according to the first embodiment of the present invention;

FIG. 10 is a diagram illustrating a guide member in an electrostatic touch assembly of a light source device for endoscope according to a second embodiment of the present invention;

FIG. 11 is a diagram illustrating a rear view of a touch board in an electrostatic touch assembly of a light source device for endoscope according to a third embodiment of the present invention; and FIG. 12 is a diagram illustrating a constituent element of an electrostatic touch assembly of a light source device for endoscope according to a fourth embodiment of the present invention.

DETAILED DESCRIPTION OF EXEMPLARY EMBODIMENTS

Exemplary embodiments of the present invention are described with reference to the accompanying drawings in detail. The same reference numbers are used throughout the drawings to refer to the same or like parts. Detailed descriptions of well-known functions and structures incorporated herein may be omitted to avoid obscuring the subject matter of the present invention.

FIG. 1 is a schematic diagram of an endoscope system according to a first embodiment of the present invention.

Referring to FIG. 1, the endoscope system according to the first embodiment of the present invention may include a light source device 300, an image processing device 200, an electronic endoscope 30 (hereinafter, referred to as an endoscope 30), an image display device 400, and an input device (not shown).

The light source device 300 may be provided with a combined white-NIR illuminator 320 and 330 to generate a white light or an excitation light in a near-infrared wavelength range so as to obtain information such as biological characteristics from an object (e.g., the internal organs of the human body) to be monitored, and transmit the generated white light or excitation light in a near-infrared wavelength range to the endoscope 30.

The image processing device 200 may control an image processing of the endoscope 30 and perform an image signal processing on an image obtained by the endoscope 30.

The endoscope 30 may be electrically detachably connected to the image processing device 200, and may be optically coupled to the light source device 300 through an optical cable. The white light or the near infrared light excitation light transmitted from the light source device 300 may be irradiated to the inside of human body, and the visible light reflected from an object, the near infrared light excitation light, and the fluorescence caused by the near infrared light excitation light may be monitored as an image by a built-in image sensor. At this time, the image sensor may convert the captured image into an image signal.

The image display device 400 and the input device may be connected to the image processing device 200. The image display device 400 may be implemented of an LCD capable of displaying the generated image or any other form capable of displaying an image as such. The input device may include a form capable of inputting various types of information of transmittable signal to the image processing device 200 or the image display device 400 such as an input button provided in the endoscope 30, or a keyboard or a mouse which is separately provided.

The endoscope 30 capable of monitoring the visible light irradiated from a monitoring target or the light in a near infrared light excitation light area may include a flexible or rigid insertion unit 30a inserted into a body cavity in which light hardly reaches, an operation unit 30b provided at the end of the insertion unit 30a, and a universal cord unit 30c extending from the side of the operation unit 30b, and electrically connected to the image processing device 200 through the universal cord unit 30c.

A main body unit of the endoscope 30 may mainly include the insertion unit 30a and the operation unit 30b, and the captured image signal and control signals may be transmitted to the image processing device 200 through a cable 3a.

An image sensor 3 forceps hole such as CMOS or CCD may be provided in a distal end of the insertion unit 30a. Since the forces hole is well known to those skilled in the art, a detailed description is omitted. In addition to the forceps holes which can be applied to a hard endoscope, it is obvious that air/water tube hole, biopsy channel hole, and the like which can be applied to a flexible endoscope may be applied.

The image sensor 3 may be electrically connected to an image sensor driver 210 through the cable 3a bundled with a plurality of signal wires.

A light guide 15 may be connected to the light source unit 500 through the universal cord unit 30c in the insertion unit 30a. The light guide 15 may include an optical system (not shown), and may guide a compound light source provided by the light source device 300, that is, a white light source and a near infrared light excitation light to be output to the end of the insertion unit.

The image processing device 200 may include an image sensor controller 215, an image sensor driver 210, a gain amplifier 230, an analog-to-digital converter (ADC) 250, a digital signal processor (DSP) 250, and a digital-to-analog converter (DAC) 290.

The image sensor driver 210 may drive an image sensor 3 embedded in the endoscope 30, and may be controlled in such a manner that a control input through the image sensor controller 215 is processed by a CPU 220.

The gain amplifier 230 may perform gain control for the image signal generated by an image pickup device 1 and the image sensor 3, and the analog-to-digital converter 250 may convert the image signal into a digital signal.

The digital signal processor 270 may perform various types of image processing such as image synthesis and white balancing for the digital image signal.

In addition, the digital signal processor 270 may adjust the image processing timing in cooperation with the CPU 220.

The digital-to-analog converter 290 may perform a process for displaying image data, for example, an analog process, and output the image data to the image display device 400.

The light source device 300 connected to the light guide 15 may include an optical coupler 310, a near infrared light source module (NIR-LD) 320, a white light source module (White-LED) 330, and a light source controller 340. A detailed structure of the light source device 300 will be described with reference to FIG. 2.

FIG. 2 is a diagram illustrating an internal structure of the light source device 300 applied to the endoscope system according to the first embodiment of the present invention.

As described above, the light source device 300 may include the optical coupler 310, the near infrared light source module 320, the white light source module 330, and the light source controller 340.

These elements may be housed in a housing of the light source device 300. On the inner side of the rear panel of the housing, at least one cooling fan 360 may be disposed to dissipate a heat generated in the components in the housing, and an adapter 352 plugged for the application of an external alternating current (AC) power may be disposed.

A direct current power supply 352 may be disposed inside the housing to be adjacent to the adapter 352 and convert the alternating current (AC) power applied to the adapter 352 into a direct current (DC) power.

The optical coupler collects and transmits the optical signals transmitted from the near infrared light source module 320 and the white light source module 330 to the endoscope. At this time, the near infrared light source module 320 and the white light source module 330 may be controlled by the light source controller 340.

Meanwhile, the light source device 300 of the present embodiment includes an electrostatic touch assembly 400 for controlling each light source through an operation. The electrostatic touch assembly 400 can perform a quick and accurate input by applying the electrostatic touch method, and can fundamentally prevent malfunction and breakdown due to various electrical unexpected situations.

Hereinafter, the electrostatic touch assembly 400 will be described in detail.

FIG. 3 is a diagram illustrating a constituent element of the electrostatic touch assembly 400 of the light source device for endoscope according to the first embodiment of the present invention.

As shown in FIG. 3, the electrostatic touch assembly 400 of the light source device for endoscope according to the first embodiment of the present invention includes a front panel 401, a masking plate 410, a touch board 420, a guide unit 440, and a light source board 430.

The front panel 401 is an element for blocking the front surface of the housing of the light source device 300, and may include a touch portion and a display portion which are exposed to the outside.

In the present embodiment, on the front surface of the front panel 401, the touch portion is formed at a position corresponding to an electrostatic touch sensor of the touch board 420 which will be described later, and the display portion is formed at a position corresponding to a light source of the light source board 430 which will be described later.

In addition, in the present embodiment, the front panel 401 is provided with a first connection portion 405 into which a part of a connection module 404 connecting the optical coupler 310 (see FIG. 2) and the endoscope provided at the outside is inserted, and a second connection portion 403 into which a power button 402 is inserted.

The touch board 420 is disposed at the rear side of the front panel 401 and includes an electrostatic touch sensor located at a position corresponding to the touch portion of the front panel 401 to sense an input generated in the touch portion.

The light source board 430 is provided behind the touch board 420 and includes a light source that irradiates light to at least one of the display portion or the touch portion of the front panel 401.

The guide unit 440 is provided between the touch board 420 and the light source board 430 and guides the light irradiated from the light source provided on the light source board 430.

The masking plate 410 is provided between the front panel 401 and the touch board 420, and is formed in such a manner that the remaining area excluding a certain area is formed to have impermeability of light so as to prevent diffusion or scattering of the light irradiated from the light source of the light source board 430.

Hereinafter, the above mentioned elements will be described in more detail.

FIG. 4 is a diagram illustrating the touch board 400, in the electrostatic touch assembly of the light source device for endoscope according to the first embodiment of the present invention.

In the present embodiment, the touch board 420 includes an electrostatic touch sensor and a through hole through which the light irradiated from the light source can pass to be irradiated to the display portion or the touch portion of the front panel 401 (see FIG. 3).

In the present embodiment, the touch board 420 includes a first touch sensor 424a for white light source module for weakening the light of the above-described white light source module 330 (see FIG. 2), a second touch sensor 424b for white light source module for strengthening the light of the white light source module 330, a first touch sensor 425a for near infrared light source module for weakening the light of the above-described near infrared light source module 320 (see FIG. 2), and a second touch sensor 425*b* for near infrared light source module for strengthening the light of the near infrared light source module 320.

In addition, a plurality of through holes are formed to include, in the present embodiment, a first through hole 421*a* formed in the area of the first touch sensor 424*a* for white light source module, a second through hole 421*b* formed in the area of the second touch sensor 424*b* for white light source module, a third through hole 411*c* formed between the first touch sensor 424*a* for white light source module and the second touch sensor 424*b* for white light source module, a fourth through hole 422*a* formed in the area of the first touch sensor 425*a* for near-infrared light source module, a fifth through hole 422*b* formed in the area of the second touch sensor 425*b* for near-infrared light source module, and a sixth through hole 412*c* formed between the first touch sensor 425*a* for near-infrared light source module and the second touch sensor 425*b* for near-infrared light source module.

Accordingly, the light irradiated to the front panel 401 through the first through hole 421*a* and the second through hole 421*b* guides a touch area for performing the operation of the white light source module 330. The light irradiated to the front panel 401 through the fourth through hole 422*a* and the fifth through hole 422*b* guides a touch area for performing the operation of the near infrared light source module 320.

In addition, the light irradiated to the front panel 401 through the third through holes 411*c* having a plurality of holes is displayed to show the intensity of the white light source module 330. The light irradiated to the front panel 401 through the sixth through holes 412*c* having a plurality of holes is displayed to show the intensity of the near infrared light source module 320.

In addition, in the present embodiment, the through hole may further include a seventh through hole 421*d* for indicating that the upper area of the touch portion is an operation area of the white light source module, and an eighth through hole 422*d* for indicating that the lower area of the touch portion is an operation area of the near infrared light source module.

In addition, in the present embodiment, a fastening hole 423 for fastening the touch board 420 may be formed on the periphery of the touch board 420.

FIG. 5 is a diagram illustrating a masking plate 400 in the electrostatic touch assembly of the light source device for endoscope according to the first embodiment of the present invention.

As described above, the masking plate 410 is provided between the front panel 401 (see FIG. 3) and the touch board 420 (see FIG. 3), and is formed in such a manner that the remaining area excluding a certain area is formed to have impermeability of light so as to prevent diffusion or scattering of the light irradiated from the light source of the light source board 430 (see FIG. 3).

In the present embodiment, the masking plate 410 performs silk printing on the remaining area excluding an area corresponding to the light source so that the light irradiated from the light source of the light source board 430 can be beautifully displayed. Accordingly, the light irradiated from the light source is transmitted only through a portion kept from the silk printing.

As described above, in the present embodiment, the masking of the masking plate 410 is achieved by performing the silk printing in a specific area. Alternatively, the masking method of the masking plate 410 may be variously implemented.

Specifically, in the present embodiment, as shown in FIG. 5, the masking plate 410 performs a masking on the remaining area excluding a first non-masking area 411*a* corresponding to the first through hole 421*a* described in FIG. 4, a second non-masking area 411*b* corresponding to the second through hole 421*b*, a third non-masking area 411*c* corresponding to the third through hole 411*c*, a fourth non-masking area 412*a* corresponding to the fourth through hole 422*a*, a fifth non-masking area 412*b* corresponding to the fifth through hole 422*b*, a sixth masking area 412*c* corresponding to the sixth through hole 412*c*, a seventh non-masking area 411*d* corresponding to the seventh through hole 421*d*, and an eighth non-masking area 412*d* corresponding to the eighth through hole 422*d*.

In addition, in the case of the masking plate 410 and the front cover 401, the masking plate 410 and the front cover 401 may be formed of various materials including plastic material such as polyethylene so that an electrical signal can be applied to the touch board 420 so as to accomplish an electrostatic touch.

FIG. 6 to FIG. 9 are diagrams illustrating the guide unit 440 and the light source board 430 in the electrostatic touch assembly of the light source device for endoscope according to the first embodiment of the present invention.

As described above, the light source board 430 is provided behind the touch board 420, and includes a board body 431 and a light source (432) for irradiating light to at least one of the display portion and the touch portion of the front panel 401.

The guide unit 440 is provided between the touch board 420 and the light source board 430 to guide the light irradiated from the light source 432 provided on the light source board 430.

In the present embodiment, the light source 432 of the light source board 430 is an LED, but it is obvious that various light sources except the LED may be used as the light source 432.

In addition, in the present embodiment, the light source 432 is provided at each position corresponding to each of the through holes of the touch board 420 (see FIG. 4), but it is not limited thereto.

In the present embodiment, the guide unit 440 includes a guide member, a fixing plate 444, and a fixing member 443.

The guide member is formed to be elongated between the touch board 420 and the light source board 430 in the front-rear direction, and has a hollow through which the light irradiated from the light source 432 passes.

In the present embodiment, the guide member includes a first guide member 441*a* corresponding to the light source 432 that irradiates light toward the first through hole 421*a* described in FIG. 4, a second guide member 441*b* corresponding to the light source 432 that irradiates light toward the second through hole 421*b*, a third guide member 441*c* corresponding to the light source 432 that irradiates light toward the third through-hole 411*c*, a fourth guide member 442*a* corresponding to the light source 432 that irradiates light toward the fourth through hole 422*a*, a fifth guide member 442*b* corresponding to the light source 432 that irradiates light toward the fifth through hole 422*b*, a sixth guide member 442*c* corresponding to the light source 432 that irradiates light toward the sixth through hole 422*c*, a seventh guide member 441*d* corresponding to the light source 432 that irradiates light toward the seventh passage hole 421d, and an eighth guide member 442d corresponding to the light source 432 that irradiates light toward the eighth through hole 422d.

In particular, the first guide member 441a, the second guide member 441b, the fourth guide member 442a, the fifth guide member 442b, the seventh guide member 441d, and the eighth guide member 442d are formed to have a larger diameter of the inner hollow than other guide members so as to cover a plurality of light sources 432.

The fixing plate 444 is an element fixed between the touch board 420 and the light source board 430 and serves to fix the guide member and the fixing member 443.

In the present embodiment, as shown in FIG. 8, the fixing plate 444 is formed in a flat plate shape, and the plurality of guide members and the fixing members 443 are inserted into and fixed to the fixing plate 444. Accordingly, the guide member is divided into a first division area A protruding forward from the fixing plate 444 and a second division area B protruding rearward.

However, unlike the present embodiment, the plurality of guide members and fixing members 443 may be integrally formed with the fixing plate 444, and may be made of the same material.

At this time, as shown in FIG. 9, the guide member has a gap G so that the front end of the first division area A may be separated from the touch board 420 so as not to be in contact with the touch board 420 and the rear end of the second division area B may be separated from the light source board 430 so as not to be in contact with the light source board 430.

The reason for this is that the light source board 430 and the touch board 420 are electrically separated from each other completely. For example, when the guide member is in direct contact with the light source board 430 and the touch board 420, malfunction may occur or breakdown may easily occur in various unexpected situations such as an electric leakage, a power failure, an overcurrent flow, or the like.

Accordingly, the present invention can prevent the above-mentioned problems by disposing the light source board 430 in the rear side of the touch board 420, fixing the guide member to the fixing plate 444 to smoothly guide the light, and preventing the guide member from being in contact with the light source board 430 and the touch board 420.

At this time, the fixing member 443 is connected between the touch board 420 and the light source board 430 to fix the fixing plate 444 while being fixed to the fixing plate 444. That is, since the fixing member 443 is directly connected to the touch board 420 and the light source board 430, the fixing member 443 may be formed of an insulating material together with the fixing plate 444.

As described above, since the light source board 430 is disposed behind the touch board 420 and they are electrically separated completely, the present invention can prevent malfunction and breakdown due to an electrical unexpected situation, and can be easily applied to an electrostatic touch-type medical device to accomplish a quick and precise input.

Alternatively, the entire guide unit 440 including the guide member, the fixing plate 444, and the fixing member 443 may be formed of an insulator. In this case, even if the guide member directly contacts the light source board 430 and the touch board 420, it is possible to prevent a malfunction from occurring in various unexpected situations such as an electric leakage, a power failure, an overcurrent flow, or the like.

Hereinafter, other embodiments of the present invention will be described.

FIG. 10 is a diagram illustrating a guide member (in the case of the present embodiment, a third guide member 441c is representatively shown) in an electrostatic touch assembly of a light source device for endoscope according to a second embodiment of the present invention.

In the case of the second embodiment of the present invention shown in FIG. 10, all elements are the same as those of the above described first embodiment, but a support member 445 is further provided at the front end of the first division area A of the guide member.

The support member 445 may be provided at the front end of the first division area A of the guide member so as to be in contact with the rear surface of the masking plate 410 and the touch board 420, thereby providing a supporting force to the masking plate 410 and the touch board 420 to prevent the masking plate 410 and the touch board 420 from being bent due to their own weight or physical external force.

At this time, the support member 445 may be formed of an elastic material so as to have a buffering property, and may be formed to have insulation so as to prevent the touch board 420 and the guide member from being electrically connected to each other.

In the present embodiment, the support member 445 is provided only at the front end of the first division area A of the guide member, but it is obvious that the support member 445 can be applied also to the rear end of the second division area A of the guide member.

FIG. 11 is a diagram illustrating a rear view of the touch board 420 in an electrostatic touch assembly of a light source device for endoscope according to a third embodiment of the present invention.

In the case of the third embodiment of the present invention shown in FIG. 11, as in the above described second embodiment, the supporting member 445 (see FIG. 10) is provided in the front end of the first division area A of the guide member, and a seating groove 426 is formed around a third through holes 421c and a sixth through holes 422c on the rear surface of the touch board 420. The seating groove 426 is formed in such a manner that a support member 445 provided at the front end of the guide member can be inserted therein, so that the touch board 420 and the light source board 430 can be aligned with each other at a precise position. Accordingly, an optical loss may not occur.

FIG. 12 is a diagram illustrating a constituent element of an electrostatic touch assembly 400 of a light source device for endoscope according to a fourth embodiment of the present invention.

In the case of the fourth embodiment of the present invention shown in FIG. 12, it has the same elements as the electrostatic touch assembly 400 of the first embodiment described in FIG. 3 as a whole, but it is different in that the masking plate 410 (see FIG. 3) is omitted.

In the present embodiment, unlike the first embodiment, the front panel 401 has a surface coated with an opaque material, and a non-masking pattern 404 is formed on the front panel 401.

The non-masking pattern 404 may be formed by a method of etching a surface coating of the front panel 401 through a laser cutting or the like. Thus, in the present embodiment, it is possible to prevent the diffusion and scattering of light only by the front panel 401 without a masking plate.

According to the present invention, the electrostatic touch assembly of light source device for endoscope and the endoscope system including the same have the following effects.

First, since the light source board is disposed in the rear side of the touch board and these boards are completely separated from each other, malfunctions and failures due to electrical unexpected situations can be fundamentally prevented.

Secondly, a quick and precise input can be performed by applying the electrostatic touch method.

Third, maintenance can be easily performed even when a defect occurs in the light source device.

Hereinabove, although the present invention has been described with reference to exemplary embodiments and the accompanying drawings, the present invention is not limited thereto, but may be variously modified and altered by those skilled in the art to which the present invention pertains without departing from the spirit and scope of the present invention claimed in the following claims.

What is claimed is:

1. A light source device for an endoscope comprising:
   a front panel;
   a touch board disposed in a rear side of the front panel and including an electrostatic touch sensor;
   a light source board disposed in a rear side of the touch board, having a plurality of light sources to irradiate light toward the front panel, the plurality of light sources including a first linear array of light sources and a second linear array of light sources, each light source of the first linear array corresponding to an intensity of a first light provided for the endoscope, each light source of the second linear array corresponding to an intensity of a second light provided for the endoscope, a wavelength of the first light being different from a wavelength of the second light; and
   a guide unit which is provided between the touch board and the light source board, and guides the light irradiated from the plurality of light sources,
   wherein the guide unit comprises a fixing plate and a plurality of guide members secured to the fixing plate and wherein each of the plurality of guide members is elongated from a front side and a rear ride of the fixing plate toward the touch board and the light source board, respectively, and has a shape of a hollow circular cylinder so that light irradiated from a corresponding one of the plurality of light sources passes therethrough,
   wherein each of the plurality of guide members is disposed to be spaced apart from the touch board and the light source board,
   wherein a support member is disposed in a gap between an upper end of one of the plurality of guide members and the touch board and formed of an electrically insulating material.

2. The light source device of claim 1, wherein the guide unit further comprises a fixing member which is disposed between the touch board and the light source board to fix the fixing plate.

3. The light source device of claim 2, wherein at least one of the fixing plate and the fixing member is formed of an electrically insulating material.

4. The light source device of claim 1, wherein a seating groove in which the supporting member is seated is formed on a rear surface of the touch board.

5. The light source device of claim 1, wherein the touch board comprises a through hole for passing the light irradiated from the plurality of light sources.

6. An endoscope system, the system comprising the light source device according to claim 1.

7. The light source device of claim 1, wherein the first light is a white light and the second light is a near-infrared light.

* * * * *